United States Patent
Wiley

Patent Number: 5,108,429
Date of Patent: Apr. 28, 1992

[54] MICROMOTOR ACTUATED ADJUSTABLE FOCUS LENS

[76] Inventor: Robert G. Wiley, 4545 Brookside Rd., Toledo, Ohio 43615

[21] Appl. No.: 667,671

[22] Filed: Mar. 11, 1991

[51] Int. Cl.$^5$ ............................................. A61F 2/16
[52] U.S. Cl. ......................................................... 623/6
[58] Field of Search .................................................. 623/6

[56] References Cited

U.S. PATENT DOCUMENTS

| | | | |
|---|---|---|---|
| 4,277,852 | 7/1981 | Poler | 623/6 |
| 4,373,218 | 2/1983 | Schachar | 623/6 |
| 4,512,039 | 4/1985 | Lieberman | 623/6 |
| 4,564,267 | 1/1986 | Nishimoto . | |
| 4,575,373 | 3/1986 | Johnson | 623/6 |
| 4,601,545 | 7/1986 | Kern | 623/4 X |
| 4,787,903 | 11/1988 | Grendahl | 623/6 |
| 4,816,031 | 3/1989 | Ploff | 623/6 |

*Primary Examiner*—Ronald Frinks
*Attorney, Agent, or Firm*—Marshall & Melhorn

[57] ABSTRACT

An adjustable focus lens apparatus includes a transparent lens body having a periphery, an attachment device adjacent to the periphery of the lens body for mounting the lens apparatus in an eye, and a plurality of micromotor devices spaced equally about and connected between the periphery of the lens body and the attachment means, each of the micromotor devices being responsive to an external control signal for selectively changing the position of an associated portion of the lens body with respect to the cornea and retina so that the functional power and astigmatism of the lens can be appropriately adjusted.

11 Claims, 3 Drawing Sheets

MICROMOTOR ACTUATED ADJUSTABLE FOCUS LENS

BACKGROUND OF THE INVENTION

The present invention relates generally to an adjustable focus lens and, in particular, to an intraocular lens system capable of varying its power and providing astigmatism correction after implantation into the eye, through the aid of externally powered and controlled micromotors.

The lens of the human eye is located centrally behind the pupil and is protected by the cornea. In the normal eye, the lens is clear and is substantially symmetrical, with opposed convex surfaces defining generally spherical sections. The lens and the cornea cooperate to focus light on the retina. The retina in turn cooperates with the nerves and the brain, so that light impinging on the retina is perceived as an image.

The light refraction which takes place in the cornea and the lens translates into an optical correction of about 60 diopters, with the cornea accounting for about 40 diopters and the lens accounting for about 20 diopters. Other refracting structures also are present in the eye, but are disregarded to simply the subject explanation.

A cataract is a condition where the normally clear lens of the eye becomes progressively opaque. This opacification typically occurs over an extended period of time, and the amount of light which passes through the lens decreases with increasing degrees of opacity. As the ability of the cataract lens to transmit light decreases, the ability of the eye to perceive images also decreases. Blindness ultimately can result. Since there are no known methods for eliminating the opacity of a cataract lens, it generally is necessary to surgically remove the opaque lens to permit the unobstructed passage of light through the pupil to the retina. The cataract lens is removed through a generally horizontal incision made at the superior part of the juncture where the cornea and sclera meet.

Once the lens has been surgically removed, light can be readily transmitted through the pupil and toward the retina. As noted above, the lens of the eye performs a significant light focusing function. Consequently, with the lens removed, the optical system of the eye is left about 20 diopters "short", and light is no longer properly focused on the retina. Eyeglasses, contact lenses and intraocular lenses are the three types of optical aids that commonly may be employed after cataract surgery to refocus the light on the retina.

Eyeglasses include lenses which are spaced from the cornea of the eye. The air space between the lens and the cornea causes an image magnification of more than 7%. Unfortunately, the brain cannot assimilate this magnification in one eye, and as a result an object appears double. This is a particular problem if the individual had only one cataract eye. Eyeglasses also substantially limit peripheral vision.

Contact lenses rest directly on the cornea of the eye, thus eliminating the air space. As a result, there is a much smaller image magnification with contact lenses than there is with eyeglasses, and the brain typically can fuse the images perceived by an eye with a contact lens and one without. Contact lenses, however, are less than perfect. For example, contact lenses are quite fragile and can be easily displaced from their proper position on the cornea. Additionally, the lenses must be periodically replaced because of protein build-up on the surface of the lens which can cause conjunctivitis. Furthermore, many of the elderly people who require cataract operations do not have the required hand coordination to properly remove or insert the lens.

Intraocular lenses first became available as optical aids to replace removed cataract lenses in the 1950's. These lenses are placed in the eye, and thus closely simulate the optics of the natural lens which they are replacing. Unlike eyeglasses, there is virtually no image distortion with a properly made and placed intraocular lens. Also, unlike contact lenses, there is no protein build-up on the intraocular lenses and the lenses require no care by the patient.

To place the lens in the eye, the surgeon ordinarily makes an incision or opening in the sclera and cornea to allow the insertion of the lens into the eye. Normally, the stabilizing loops of the attachment members of the lens are flexible and can be bent, if necessary, to pass through the opening. Accordingly, the minimum length of opening which must be made and is ordinarily determined by the diameter of the substantially rigid lens body, or optic, usually having a circular periphery. It is, of course, desirable to make the opening into the eye as small as possible to minimize the risk of damage to the eye. In the past few years, some lenses have been made of flexible material like silicone that can be folded so as to go into the eye through a smaller opening.

The current practice in the implantation of intraocular lenses is to replace a normal crystalline human lens of the eye removed at the time of surgery, such as in cataract surgery, with an intraocular lens such as an anterior chamber lens or posterior chamber lens formed of appropriate biocompatible material such as PMMA (polymethyl methacrylate) material. However, one of the present problems with intraocular lenses is that it is necessary to decide on the power of the lens preoperatively. This can be accomplished, for example, by performing an ultrasound scan and/or evaluating the patient's refraction preoperatively and then making a clinical estimate of the proper power of the lens in order to determine proper refraction of the eye. However, even with the best medical techniques and sophisticated optical instruments available, ophthalmologists have never been able to correct for accommodation which is the ability to change the focus of vision from distance to near vision and there is no lens system that can be adjusted after implantation for even minor changes in spherical or astigmatic power. Thus, most patients, following routine lens implantation, require the use of glasses for precisely focused distance and near vision.

The prior art intraocular lens typically is either of plano-convex construction or double convex construction, with each curved surface defining a spherical section. The lens is placed in the eye through the same incision which is made to remove the cataract lens. As noted above, this incision typically is made along the superior part of the eye near the juncture of the cornea and the sclera. About one third of all postoperative patients will have significant astigmatism and, approximately one third will need a spherical adjustment in their postoperative glasses to see clearly. In virtually all instances, the surgery itself induces astigmatism which fluctuates significantly during the first few weeks, or even months, after the surgery.

Postoperative induced astigmatism is attributable to the healing characteristics of the eye adjacent the incision through which the cataract lens is removed and the intraocular lens is inserted. More particularly, the incision in the eye tends to heal slowly. The incision in the eye may take eight weeks to a year to properly heal. During the period when the eye is healing, the wound area tends to spread and thus a cornea that may have been spherical before surgery is made other than spherical. Since the incision is generally horizontally aligned, the spreading is generally along the vertical meridian. Initially, after the surgery, the cornea is relatively steep in the vertical meridian. As the eye heals, the cornea becomes relatively flat in the vertical meridian. Consequently, the optical system of the eye, which may previously have been spherical, becomes "toric" with the vertical meridian of the optical system providing a different optical power than the horizontal meridian. This non-spherical configuration of the optic system is generally referred to as "astigmatism".

The degree of this induced astigmatism varies according to the type of incision made, the presence or absence of sutures or the number and type of sutures used, the technical skill and care employed by the surgeon, and the physical attributes of the eye. For example, the use of a fine nylon suturing material typically results in a smaller deviation from sphericity than the use of silk or absorbable sutures. Generally, the induced astigmatism varies from 0.5 to 5 diopters. The initial postoperative astigmatism is generally caused by the steepening of the vertical meridian. Late astigmatism is caused by the flattening of the vertical meridian of the cornea. The orientation and amount of postoperative astigmatism are, in most cases, not accurately predictable. Postoperative astigmatism typically is corrected by prescription eyeglasses which need to be changed periodically as the eye heals.

In some cases, despite the best efforts of the ophthalmologist, the lens surgically placed in the patient's eye does not provide good distance visual acuity due to spherical miscalculations and due to the changing astigmatic requirements. Since the surgery itself can cause significant change in the amount and axis of the astigmatism present after cataract surgery, the exact amount and axis of astigmatism can not be accurately determined until sometime, usually several weeks or months, after the surgery. Since the old intraocular lens can not be readily removed and a new intraocular lens with a different power surgically installed without unduly jeopardizing the patient's vision, the patient must rely on spectacles to provide accurately focused visual acuity. In other words, although the need to wear heavy, bulky, higher power spectacles is eliminated, the patient nevertheless usually must wear spectacles for best focused vision.

Several attempts have been made to provide an intraocular lens which corrects for the astigmatism expected after surgery or can be varied in spherical power after implantation. U.S. Pat. No. 4,575,373 discloses a laser adjustable intraocular lens which utilizes a laser to alter, in situ, the power of an implanted intraocular lens. The outer ring of the lens is manufactured of a non-toxic heat shrinkable colored plastic material to permit selective absorption of laser energy, thereby causing the shape of the lens to change increasing the power irreversibly.

U.S. Pat. No. 4,816,031 discloses an intraocular lens system including a PMMA lens implant, a second soft and pliable lens positioned thereover, and electromechanical circuitry for regulating the distance between the two lenses, thereby providing for adjustment of the focal point of the lens system.

U.S. Pat. No. 4,512,039 discloses an intraocular lens for offsetting postoperative astigmatism having the finally placed vertical meridian optically weaker than the horizontal meridian. Proper placement is ensured b disposing the haptics along the vertical meridian.

U.S. Pat. No. 4,277,852 discloses an intraocular lens with astigmatism correction combined with a supporting mount or haptic structure to assure correct optical orientation of the implant.

Several attempts have been made to provide a variable power intraocular lens, which power varies according to an application of a force external to the lens, for correcting the astigmatism expected after surgery. U.S. Pat. No. 4,787,903 discloses an intraocular lens including an annular Fresnel (prism) lens, made of a high index of refraction material such as polymethylmethacrylate. A composite material overlays the Fresnel elements to provide a smooth external surface and is made of a suitable material, for example, crystalline lattice or liquid crystal material, which changes the index of refraction when excited with electrical power or radiant energy. The lens carries a complementary loop or other energy pick-up device, for receiving the power from an electric field generated by an external power source feeding a coupling loop. The coupling loop can be carried in an eyeglass frame, implanted about the eye socket or positioned by the lens wearer or an ophthalmologist. It is stated in the patent specification that some overlay materials can be switchable between more than two states, each with a different index of refraction, while other materials will provide a continuously variable index of refraction which may be stable or may return to an initial value when the energy is removed. However, such materials are not identified in the patent.

U.S. Pat. No. 4,601,545 discloses a variable power lens system including an optically active molecular material such as liquid crystals. A variable gradient index of refraction is achieved by applying a controlled stimulus field, such as a geometrically configured matrix of electrical voltages, to the lens. A corresponding matrix of horizontal and vertical conductors applies the electrostatic field produced by the applied voltage to be selectively controlled at discrete points so that a gradient index of refraction is produced.

U.S. Pat. No. 4,564,267 discloses a variable focal length lens which can be electrically controlled by applying an electric field to a compound lens including at least one lens formed of electrooptic crystals. The electrooptic crystals are juxtaposed between first and second transparent electrode plates each comprising a plurality of concentric annular transparent electrodes. A power source connected to the electrodes generates an electric field across the crystals creating a refracting index distribution having a lens action. The electric field effectuates a change in the focal length of the lens which varies according to the potential imparted.

U.S. Pat. No. 4,373,218 discloses a variable power intraocular lens including a fluid expandable sac for containing a liquid crystal material that is used in combination with an electrode and a microprocessor for changing the index of refraction of the lens. An electrode is located in a ciliary body to provide an input signal that is proportional to a desired accommodation to a microprocessor which can be implanted into a sclera of a human eye. The microprocessor produces a potential across the liquid crystal material to control the index of refraction to obtain the desired accommodation based upon the relative position of the eyes. The voltage output of the microprocessor is applied to electrodes which can be a thin transparent material forming a coating on the interior of the fluid expandable sac.

SUMMARY OF THE INVENTION

The present invention concerns an adjustable focus lens which can be formed as an intraocular lens implanted in the human eye. The lens apparatus includes a transparent and flexible lens body having a periphery; means for mounting the lens body in an eye such as legs, a loop or a ring; and a selective position and orientation control device in the form of a plurality of micromotor means spaced equally about and connected between the periphery of the lens body and the mounting means, each of the micromotor means being responsive to a predetermined external source of energy (such as ultrasound) for selectively changing the position of the lens body or a portion thereof in the eye for power and astigmatism modification.

In one embodiment, the means for mounting includes an expandable and contractible inner ring formed at the periphery of the lens body and a relatively rigid outer ring, the micromotor means being connected between the outer ring and the inner ring. In another embodiment, the means for mounting can be a pair of loops having ends connected to a periphery of the lens body by the micromotor means. In yet another embodiment, the means for mounting is a pair of hooks having ends attached to the periphery of the lens body by the micromotor means.

The micromotor means can be a linear positioning device having a base attached to the outer ring, loop or hook and an extendable rod attached to the lens body. Power for the micromotor means can be provided from an external source which can be ultrasound, static electricity, magnetic field, laser beam, etc. In addition, potential energy can be stored, for example, in the outer ring or the linear positioning device for use after implantation in response to an external triggering device.

In an intraocular lens application, the postoperative vision of the lens implant recipient may be repeatably corrected or adjusted to near perfectly focused vision. The changed power and/or astigmatism correction of the lens remains stable until such time the implant recipient needs to have the external force field applied to correct a deviation from perfect vision caused by other sources (such as the changes in astigmatism common in the healing process) thus eliminating the need for changes in glasses to keep the eye in good focus. Furthermore, due to the passive restraint system in place, the lens according to the present invention is stable, retaining the focus and/or astigmatism correction after the external force field has been removed. Such lens does not require a continuous power source, nor a power source being coupled to the lens material by circuitry and a matrix of electrodes, nor power coupling loops to supply continuous power to the lens. The lens can be easily adjustable: adding or subtracting spherical lens power or adding or subtracting astigmatic lens power thus fine tuning the lens focus as needed as often as necessary over the life of the patient.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
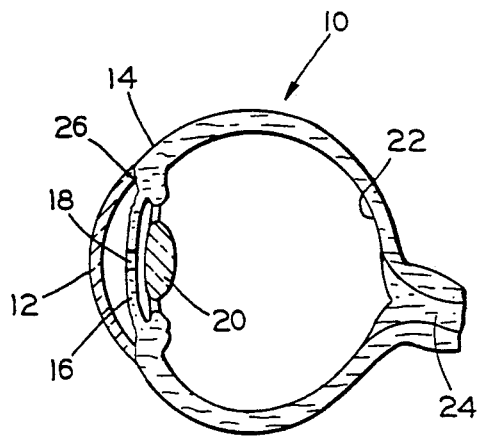
FIG. 1 is a cross-sectional side elevation view of a normal human eye prior to removal of the natural lens.

Referring to the FIG. 1, there is illustrated a normal human eye generally indicated by the reference numeral 10. The eye 10 includes a cornea 12 covering an opening in a generally spherical sclera 14. Positioned interiorly of the cornea 12 in the opening in the sclera 14 is an iris 16 having a pupil 18. Positioned behind the pupil 18 is a lens 20 which focuses entering light onto a retina 22 on the interior surface of the eye, the retina being connected to the brain (not shown) by an optic nerve 24. The lens 20 is located centrally behind the pupil 18 and is protected by the cornea 12. In the normal eye 10, the lens 20 is clear and is substantially symmetrical, with opposed convex surfaces defining generally spherical sections. The lens 20 and the cornea 12 cooperate to focus incoming light on the retina 22. The retina 22 in turn cooperates with the optic nerve 24 and the brain, so that light impinging on the retina 22 is perceived as an image.

The light refraction which takes place in the cornea 12 and the lens 20 translates into an optical correction of about sixty diopters, with the cornea 12 accounting for about forty diopters and the lens 20 accounting for about twenty diopters. Other refracting structures also are present in the eye 10, but are disregarded here to simplify the explanation.

A cataract is a condition where the normally clear natural lens 20 of the eye 10 becomes progressively opaque. This opacification typically occurs over an extended period of time, and the amount of light which passes through the lens 20 decreases with increasing degrees of opacity. As the ability of the cataract lens 20 to transmit light decreases, the ability of the eye 10 to perceive to images also decreases. Ultimately, blindness can result. Since there are no known methods for eliminating the opacity of a cataract lens 20, it generally is necessary to surgically remove the opaque lens 20 to permit the unobstructed passage of light through the pupil 18 to the retina 22. The cataract lens 20 is removed through a generally horizontal incision made at the superior part of a juncture 26 where the cornea 12 and the sclera 14 meet.

Figure 2:
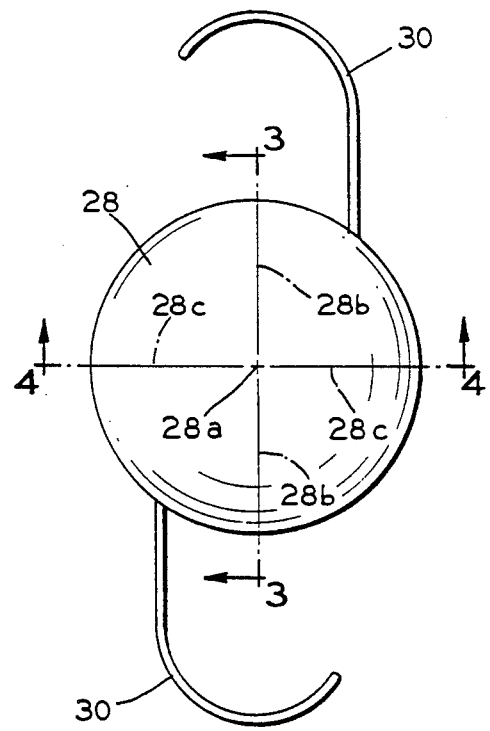
FIG. 2 is a front elevation view of a typical prior art intraocular lens.

Once the cataractous lens 20 has been surgically removed, light can be readily transmitted through the pupil 18 and toward the retina 22. However, the lens 20 performs a significant light focusing function. Consequently, with the lens 20 removed, the optical system of the eye is left about twenty diopters "short", and light is no longer properly focused on the retina 22. When a lens 20 is removed to eliminate cataracts, it must be replaced by an artificial lens. An intraocular lens, such as a prior art intraocular lens 28 shown in the FIG. 2, is commonly employed after cataract surgery to refocus the light on the retina 22.

Figure 5:
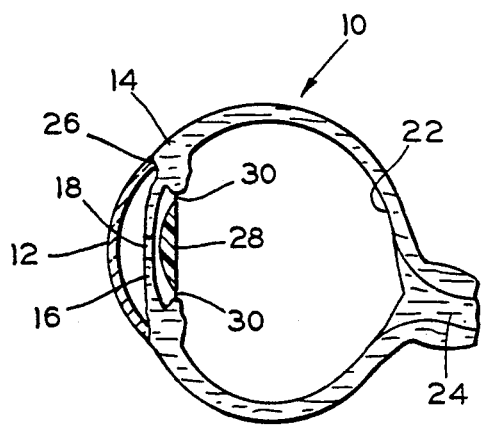
FIG. 5 is a cross-sectional side elevation view of the human eye shown in the FIG. 1 after the insertion of the intraocular lens shown in the FIG. 2.

The intraocular lens 28 can be constructed of any biologically inert, transparent material suitable for optical correction such as, for example, silicone. The lens 28 is a section of a sphere, generally circular as viewed from the front with a diameter of approximately six millimeters. A pair of legs 30, also known as haptics, function to support the lens 28 in the proper position in the posterior chamber of the eye 10 (FIG. 5). Each haptic 30 extends approximately four millimeters from a straight end attached to a periphery of the lens 28 to a curved end to be attached to the eye. Thus, the total width of the lens 28 and the haptics 30 is approximately fourteen millimeters.

The intraocular lens 28 is inserted behind the iris 16 as illustrated in the FIG. 5. This type of lens is referred to as a posterior chamber lens, the latest and most popular of the many designs of intraocular lenses.

It should be understood that the prior art lens 28 can be manufactured for positions in the eye other than the posterior chamber. For example, the lens 28 can be placed in the anterior chamber, the area between the cornea 12 and the iris 16. However, such positioning is sometimes considered undesirable because positioning the lens very close to the cornea may result in traumatization of the endothelium of the cornea.

A problem associated with the proper implantation of an intraocular lens is the accurate postoperative determination of the exact prescriptive or refracting power of the lens to be placed in the eye of the patient. The ophthalmologist or optometrist can, for example, attempt to estimate the prescriptive power of the natural lens 20 of the patient and, through the use of various measuring devices, e.g. ultrasound, measure the depth and diameter of the eye 10. These measurements in conjunction with clinical experience permit the ophthalmologist or optometrist to relatively accurately determine the proper refraction or power of the intraocular lens 28 to be implanted.

In some cases however, despite the best efforts of the ophthalmologist or optometrist, the lens surgically placed in the eye is not the correct dioptric power and the patient does not obtain good unaided visual acuity. During the postoperative healing period, the patient has a variable amount of astigmatism, a refracting defect which prevents focusing of sharp distinct images. Some astigmatism present after cataract surgery is due to the surgical incision and changes in corneal curvature as a consequence of the healing of the incision.

Figure 3:
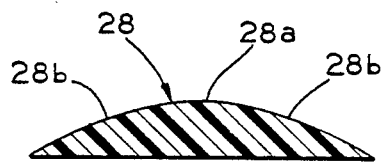
FIG. 3 is a cross-sectional view of the lens shown in the FIG. 2 taken along the line 3—3 on the vertical meridian.
Figure 4:
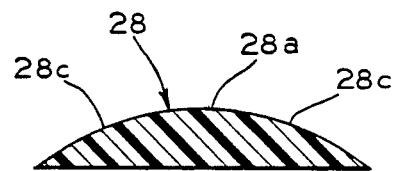
FIG. 4 is a cross-sectional view of the lens shown in the FIG. 2 taken along the line 4—4 on the horizontal meridian.

The curvature in the lens 28 can be formed asymmetric such that a vertical meridian, along a cross section line 3—3 as illustrated in the FIG. 3, is optically weaker (longer diameter for less curvature) than an horizontal meridian along a cross section line 4—4 as illustrated in the FIG. 4. The thickness of the lens 28 at a center 28a remains constant. Thus, the difference in the respective optical strengths of vertical and horizontal meridians is created by different structural contours (such as different radii of curvature), 28b and 28c, in the vertical and horizontal meridians respectively resulting in different light refracting characteristics. Thus, the lens 28 defines a section of a sphere. In order to properly align the lens 28 at the time of insertion in the eye, the haptics 30 are offset from and extend generally parallel to the vertical meridian. Thus, as explained above, the prior art intraocular lens 28 has a fixed correction and angle for astigmatic power as well as a fixed spherical power.

In the FIGS. 6-9, there are shown various embodiments of a micromotor actuated adjustable focus intraocular lens apparatus according to the present invention. In the FIG. 6, the apparatus is generally indicated by a reference numeral 32, which lens is provided with means for selectively changing the functional spherical power of the lens and for selectively providing correction for astigmatism. The lens apparatus 32 includes a central lens body 34 formed of a transparent flexible material, such as a silicone or the like. The lens body 34 is generally disc-shaped and has a convex surface adapted to be centered in the pupil of an eye and may have a concave, planar or convex rear surface. A periphery 36 of the lens body 34 can be formed as an inner ring of any suitable material to provide a stable mounting means for actuators. For example, the periphery 36 could be molded integral with the lens body 34, but thicker in cross section.

A plurality of spaced micromotors 38 extend radially inwardly toward the center of the lens body 34. The micromotors 38 each have an inner end attached to the inner ring 36 and an outer end attached to an outer ring 40 which extends concentrically about the lens body 34. The outer ring 40 is made from a relatively rigid material and provides a fixed support for the micromotors 38 and the lens body 34. The outer ring 40 supports the lens apparatus 32 in the proper position in the eye.

Figure 6:
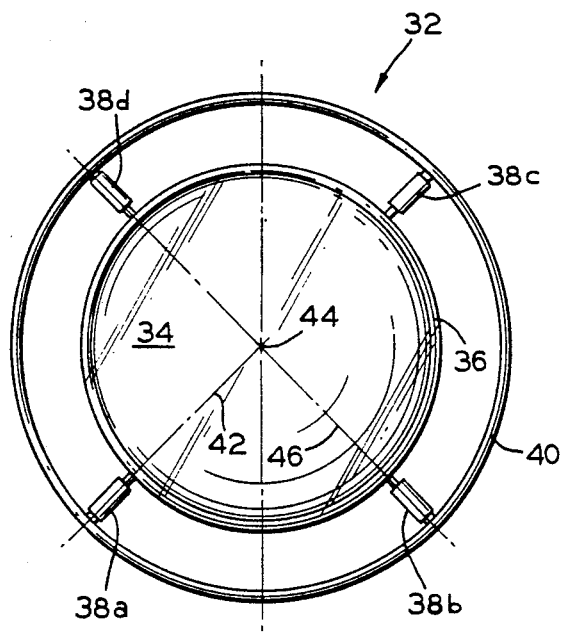
FIG. 6 is a front elevation view of an intraocular lens apparatus having a ring type attachment device in accordance with the present invention.

In the FIG. 6, if it is assumed that the lens assembly 32 is being viewed from the front, outside the cornea of the eye, then movement of the lens body 34 toward the viewer, the anterior direction, will increase the functional power of the lens based upon well known optical principles. Conversely, movement the lens body 34 toward the optic nerve, the posterior direction, will decrease the functional power of the lens assembly 32. The micromotors 38 cooperate with the inner ring 36 and the outer ring 40 to provide selective adjustment of the power of the lens from outside the eye. Each of the micromotors 38 can be powered by an external energy source, not shown, such as a source of ultrasonic energy at a frequency which causes extension action by the micromotors 38 equally moving the lens body 34 forward in a horizontal direction while maintaining the lens body 34 in a generally vertical plane. The application of energy at a different frequency will cause retraction action by the micromotors 38 equally moving the lens body 34 posteriorly in the horizontal direction while maintaining the lens body in the generally vertical plane.

There is shown in the FIG. 6 a radius 42 of the lens apparatus 32 extending outwardly from a center point 44 of the lens body 34 through one of the micromotors 38, a micromotor 38a. Any rotation of the lens body 34 about an axis in the plane normal to the path of light rays between the cornea 12 and the optic nerve 24 (FIG. 5) will cause an induced astigmatic effect for modifying astigmatism. If an irregular astigmatism which by its nature is segmental were located along the radius 42 and the lens body was made of flexible material, the micromotor 38a could be actuated to bend a segment of the lens body 34 relative to the remaining portion of the lens body. The more common variety of astigmatism is regular astigmatism which extends completely across the optical axis. Correcting regular astigmatism oriented along an axis 46 can be adjusted by activating the micromotors 38a in an anterior direction and 38c in a posterior direction, or visa versa.

Prior to implantation in the eye, the optical properties of the lens could be measured and stored in a computer, for example, with reference to the various combinations of actuation of the micromotors. After implantation in the eye, the data stored in the computer can be utilized along with postoperative information to guide the actuation of the micromotors to produce the desired dioptic power and astigmatic modifications. To correct for irregular and regular astigmatism and for dioptic power adjustments, micromotor manipulation may be aided by a computer program that calculates the amount of activation to be used on each micromotor by analyzing information from the following sources: corneal topography, corneal curvature radii, the refraction, axial length of the eye, and other ocular and lens data.

Figure 7:
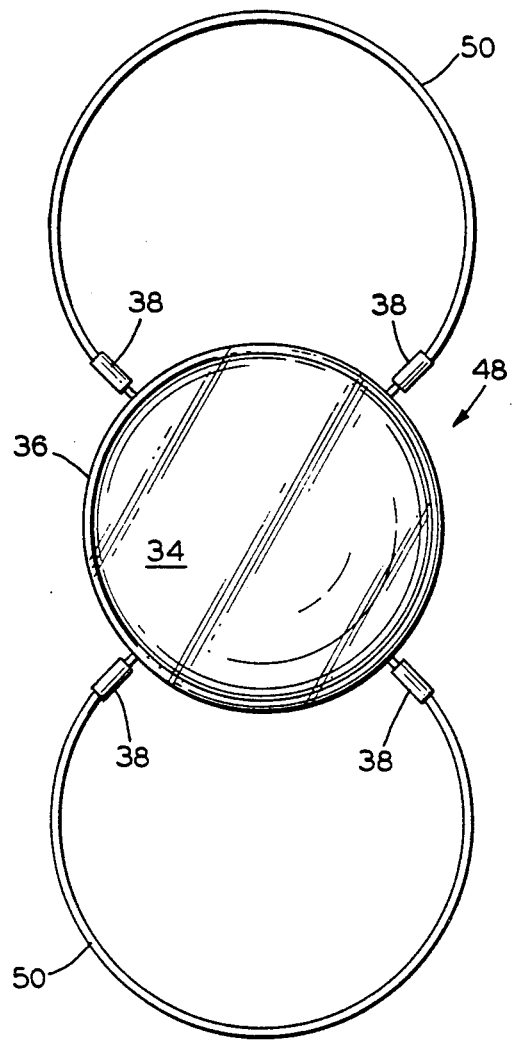
FIG. 7 is a front elevation view of an alternate embodiment of the intraocular lens apparatus according to the present invention having a pair of loop type attachment devices.

There is illustrated in the FIG. 7 an alternate embodiment of the lens apparatus 32. A lens apparatus 48 includes the lens body 34 having the inner ring 36 attached to a plurality of micromotors 38. An attachment means in the form of a pair of loops 50 is attached to the lens body with an end of each of the loops 50 attached to an associated one of the micromotors 38. The lens apparatus 48 operates in a manner similar to the lens apparatus 32.

Figure 8:
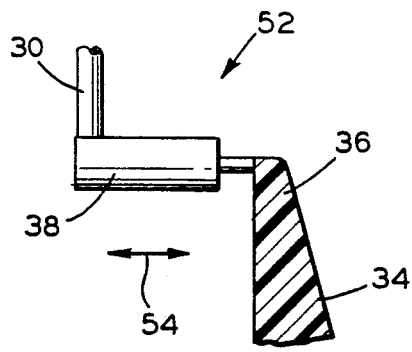
FIG. 8 is an enlarged cross-sectional view of a portion of a second alternate embodiment of the intraocular lens apparatus according to the present invention having a leg type attachment device.

In the FIG. 8 there is illustrated an alternate embodiment of the present invention. A lens apparatus 52 includes the lens body 34 having the periphery 36 thereof attached to one end of a generally horizontally extending one of the micromotors 38. The opposite end of the micromotor 38 is attached to one end of one of the legs 30. Thus, the micromotor 38 can be actuated in the direction of an arrow 54 thus changing the focal power and/or the astigmatic power of the lens body 34.

Figure 9:
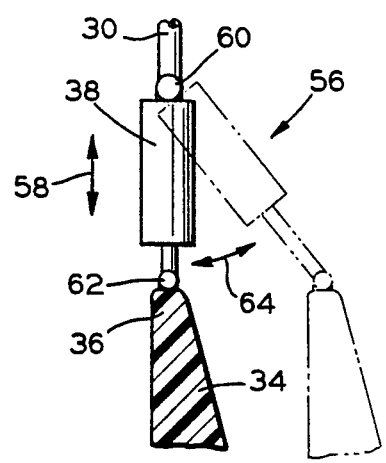
FIG. 9 is an enlarged cross-sectional view of a portion of a third alternate embodiment of the intraocular lens apparatus according to the present invention having a leg type attachment device.

Referring to the FIG. 9, there is shown an enlarged cross-sectional view of another alternate embodiment of the present invention. A lens apparatus 56 includes the lens body 34 having the periphery 36 thereof attached to one end of a generally vertically extending one of the micromotors 38. The opposite end of the micromotor 38 is attached to one end of one of the legs 30. Thus, the micromotor 38 can be actuated in the direction of an arrow 58 to change the focal power and/or the astigmatic power of the lens body 34. If one end of the micromotor 38 is attached to the leg 30 by a pivot means 60 and the other end of the micromotor 38 is attached to the ring 36 by a pivot means 62, then the micromotor 38 can be actuated to extend, as shown in phantom, and move along a curved path as illustrated by an arrow 64.

Figure 10:
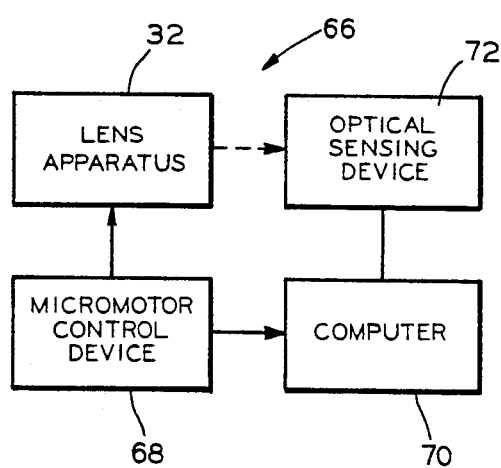
FIG. 10 is a block diagram of a system for testing and storing data to be used to selectively position and orient the intraocular lens apparatus according to the present invention.

The FIG. 10 is a block diagram of a system 66 for testing and storing data to be used to selectively position and orient the intraocular lens apparatus 32. A micromotor control device 68 individually controls the actuation of each of the micromotors provided in the lens apparatus 32. The micromotor control device 68 generates control signals and/or the power necessary to actuate the micromotors. At the same time, the control device 68 generates information signals to a computer 70 identifying which micromotors have been actuated. An optical sensing device 72 is provided for sensing the optical properties of the lens apparatus 32 and providing such information to the computer 70. The computer 70 stores the optical information from the sensing device in association with the control information from the control device 68 for later use.

Figure 11:
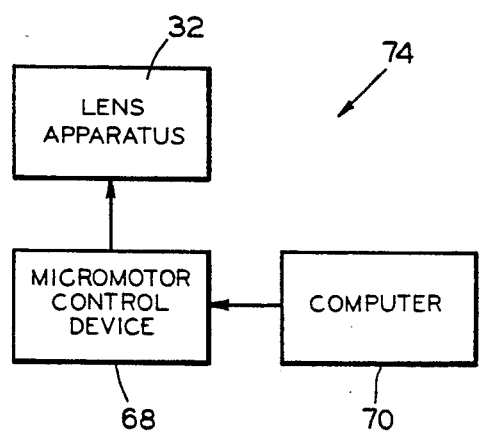
FIG. 11 is a block diagram of a system for selectively positioning and orienting the intraocular lens apparatus according to the present invention after implantation in the eye.

The FIG. 11 is a block diagram of a system 74 for selectively positioning and orientating the intraocular lens apparatus 32 after implantation in the eye. When it is desired to change the functional power of the lens apparatus 32 and/or provide an astigmatism correction, the computer 70 will provide the necessary output signals to the micromotor device 68. The micromotor device 68 responds to the information from the computer 70 to generate the appropriate control signals and/or power necessary to actuate a predetermined combination of the micromotors in the lens apparatus 32 to produce the desired results.

Not only can the adjustment process described with respect to the FIGS. 10 and 11 be performed in a doctor's office or medical facility, for example, but the system for selectively positioning and orientating the intraocular lens apparatus could be provided for use by the patient. The computer 70 and the micromotor control device 68 could be located in a pair of eye glass frames with controls for use by the patient. When the patient sensed a need to change the functional power, the patient would put on the glass frames, push an appropriate button, and the intraocular lens apparatus would be automatically changed. One example of such use could be when the patient wished to switch from distance vision to vision for close work such as reading or watch repair. The system according to the present invention could be provided so that it could be manipulated by the patient to self adjust the intraocular lens apparatus even providing adjustments for good vision as close as six inches from the work.

The utilization of such an intraocular lens in accordance with the present invention may eliminate the need of the recovering cataract patient to wear eye glasses or contact lenses. The elimination of the glasses or contact lenses amounts to an immense benefit to the recovering cataract patient, many of whom are elderly, sometimes forgetful, and many have financial and physical hardships.

The adjustable focus lens of the present invention has a variety of applications, in addition to the application as an intraocular lens. For example, the adjustable focus lens can be used as a camera lens. The lens could be used as an alternative to or in conjunction with cameras having either a fixed lens, an adjustable lens, or a plurality of interchangeable lenses.

In accordance With the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. An adjustable focus intraocular lens apparatus for implantation into an eye comprising:
    a transparent lens body having a periphery;
    an attachment means adjacent said periphery of said lens body; and
    micromotor means connected between said periphery of said lens body and said attachment means and responsive to an external control signal for selectively and reversibly changing the position of said lens body with respect to a cornea and retina of an eye thereby adjusting the functional power and astigmatism correction of said lens body in the eye.

2. The lens apparatus according to claim 1 wherein said periphery of said lens body has an inner ring formed thereon, said attachment means is formed as an outer ring about said inner ring and said micromotor means is connected between said inner ring and said outer ring.

3. The lens apparatus according to claim 1 wherein said periphery of said lens body has an inner ring formed thereon, said attachment means is formed as a pair of loops and said micromotor means is connected between said inner ring and ends of said loops.

4. The lens apparatus according to claim 1 wherein said periphery of said lens body has an inner ring formed thereon, said attachment means is formed as at least a pair of loops and said micromotor means is connected between said inner ring and an end of each of said loops.

5. The lens apparatus according to claim 1 wherein said micrometer means moves said lens body forward and back along a path generally parallel to a path of travel of light rays between the cornea and the retina in the eye.

6. The lens apparatus according to claim 1 wherein said micrometer means is connected to said periphery of said lens body and said attachment means by pivot means for movement of said lens body forward and back along a generally arcuate path of travel in the eye.

7. An adjustable focus intraocular lens apparatus for implantation into an eye comprising:
    a transparent lens body having a periphery;
    an attachment means adjacent said periphery of said lens body; and
    a plurality of micromotors connected between said periphery of said lens body and said attachment means and each responsive to an external control signal for selectively and reversibly changing the position of an associated portion of said lens body with respect to a cornea and retina of an eye thereby adjusting the functional power and astigmatism correction of said lens body in the eye.

8. The lens apparatus according to claim 7 wherein each said micromotor is connected to said periphery of said lens body and said attachment means by pivot means for movement forward and back of said associated lens body portion along a generally arcuate path of travel in the eye.

9. An adjustable focus intraocular lens system for selectively positioning and orienting a lens body after implantation into an eye comprising:
    a transparent lens body having a periphery;
    an attachment means adjacent said periphery of said lens body;
    a plurality of micromotors connected between said periphery of said lens body and said attachment means and each responsive to an external control signal for selectively changing the position of an associated portion of said lens body with respect to a cornea and retina of an eye thereby adjusting the functional power and astigmatism correction of said lens body in the eye;
    a control device external to the eye for generating said control signals; and
    a computer connected to said micromotor control device, said computer generating control data to said control device representing desired functional power adjustments and astigmatism corrections, said control device being responsive to said control data for generating said control signals.

10. The system according to claim 9 including an optical sensing device connected to said computer for collecting optical data representing optical properties of said lens body and an eye and generating said optical data to said computer and wherein said control device generates actuation data representing said control signals to said computer, said computer associating said actuation data with said optical data for generating said control data.

11. The system according to claim 9 wherein said micromotor control device is adapted to be worn by a person having said lens body, said attachment means and said micromotors implanted in his eye.

* * * * *